United States Patent
Pettersson et al.

(10) Patent No.: US 9,265,720 B2
(45) Date of Patent: Feb. 23, 2016

(54) PHARMACEUTICAL FORMULATIONS USEFUL IN THE TREATMENT OF INSOMNIA

(75) Inventors: Anders Pettersson, Kode (SE); Christer Nyström, Stockholm (SE); Susanne Bredenberg, Uppsala (SE)

(73) Assignee: Orexo AB, Uppsala (SE)

( * ) Notice: Subject to any disclaimer, the term of this patent is extended or adjusted under 35 U.S.C. 154(b) by 1660 days.

(21) Appl. No.: 11/666,361

(22) PCT Filed: Oct. 26, 2005

(86) PCT No.: PCT/GB2005/004147
§ 371 (c)(1),
(2), (4) Date: Feb. 11, 2008

(87) PCT Pub. No.: WO2006/046041
PCT Pub. Date: May 4, 2006

(65) Prior Publication Data
US 2008/0311208 A1    Dec. 18, 2008

(30) Foreign Application Priority Data

Oct. 27, 2004  (GB) .................................. 0423800.2

(51) Int. Cl.
| A61K 9/14 | (2006.01) |
| C07D 471/04 | (2006.01) |
| A61P 25/20 | (2006.01) |
| A61K 47/26 | (2006.01) |
| A61K 9/00 | (2006.01) |
| A61K 31/44 | (2006.01) |

(52) U.S. Cl.
CPC ............... *A61K 9/0002* (2013.01); *A61K 31/44* (2013.01)

(58) Field of Classification Search
CPC .............................. A61K 31/44; A61K 9/0002
See application file for complete search history.

(56) References Cited

U.S. PATENT DOCUMENTS

| 4,574,080 | A | 3/1986 | Roswall et al. | |
| 6,514,531 | B1 | 2/2003 | Alaux et al. | 424/468 |
| 6,638,535 | B2 | 10/2003 | Lemmens et al. | 424/489 |
| 6,759,059 | B1 | 7/2004 | Pettersson et al. | |
| 6,761,910 | B1 | 7/2004 | Pettersson et al. | |
| 7,910,132 | B2 | 3/2011 | Pettersson et al. | |
| 2005/0013857 | A1* | 1/2005 | Fu et al. | 424/464 |
| 2005/0215521 | A1* | 9/2005 | Lalji et al. | 514/58 |
| 2005/0226925 | A1* | 10/2005 | Singh | 424/464 |

FOREIGN PATENT DOCUMENTS

| CN | 1 290 525 | 4/2001 |
| CN | 1 418 631 | 5/2003 |
| CN | 1418631 A | 5/2003 |
| EP | 0324725 | 7/1989 |
| EP | 1 260 216 | 11/2002 |
| EP | 1488811 A1 | 12/2004 |
| EP | 1552851 A1 | 7/2005 |
| JP | 6065103 A | 3/1994 |
| WO | WO 9004962 | 5/1990 |
| WO | WO 00/16750 | 3/2000 |
| WO | WO 00/33835 | 6/2000 |
| WO | WO-0057858 A1 | 10/2000 |
| WO | WO 01/30391 | 5/2001 |
| WO | WO-0130391 A2 | 5/2001 |
| WO | WO-02094230 A1 | 11/2002 |
| WO | WO 03/059349 | 7/2003 |
| WO | WO-03103629 A1 | 12/2003 |
| WO | WO-2004045589 A1 | 6/2004 |
| WO | WO 2004-091585 | 10/2004 |
| WO | WO-2004091585 A1 | 10/2004 |
| WO | WO-2005032519 A1 | 4/2005 |
| WO | WO-2005079761 A1 | 9/2005 |
| WO | WO-2005089768 A1 | 9/2005 |

OTHER PUBLICATIONS

British National Formulary, vol. 48, pp. 174-175.
Holm et al., "An Update of its Pharmacology, Therapeutic Efficacy and Tolerability in the Treatment of Insomnia", Drugs, 59(4):865-889 (2000).
Darcourt et al., "The Safety and tolerability of zolpidem—an update", Journal of Psychopharmacology, 13(1):81-93 (1999).
Terzano et al., "New Drugs for Insomnia", Drug Safety, 26(4):261-282(2003).
Salva et al., "Clinical Pharmacokinetics and Pharmacodynamics of Zolpidem", Clin. Pharmacokinet., 29(3):142-153 (1995).
Drover et al., "Pharmacokinetics, Pharmacodynamics, and Relative Pharmacokinetic/Pharmacodynamic Profiles of Zaleplon and Zolpidem".
Nystrom et al., The use of ordered mixtures for improving the dissolution rate of low soluility compounds, J. Pharm. Pharmacol., 38:161-165 (1986).
Goodman & Gilman's, The Pharmacological Basis of Therapeutics, 10th edition, Eds. Hardman and Limbird, McGraw-Gill (2001), pp. 18-29 (Attachment A to Amendment A).
List of Psychotropic Substances Under International Control, prepared by the International Narcotics Control Board (Attachment B to Amendment A).

(Continued)

*Primary Examiner* — Suzanne Ziska
*Assistant Examiner* — Thurman Wheeler
(74) *Attorney, Agent, or Firm* — Covington & Burling LLP

(57) ABSTRACT

There is provided a formulation suitable for transmucosal administration comprising a short acting hypnotic drug, which formulation provides a measurable plasma concentration of drug within 10 minutes of administration. The formulation is capable of providing sleep on demand, and preferably comprises particles of drug, for example zolpidem or a pharmaceutically-acceptable salt thereof and a mucoadhesion promoting agent, such as sodium carboxymethylcellulose, which particles of drug and mucoadhesive are presented upon the surface of larger carrier particles.

26 Claims, 1 Drawing Sheet

(56) References Cited

OTHER PUBLICATIONS de Wit et al, Psychopharmacology, 107, 352 (1992) (Attachment C to Amendment A).

Vogt et al, Eur J. Clin. Pharmacol, 46, 319 (1994) (Attachment D to Amendment A).

Kroboth et al, J. Clin. Psychopharmacol., 15,259 ( 995) (Attachment E to Amendment A).

Roth et al, In Hum. Pychopharmacol, Clin. Exp. 23, 12, (2008) (Attachment F to Amendment A).

Staner et al., Sleep Medic ne, 10, 616 (2009) (Attachment G to Amendment A).

On-line Rx that lists data for Ambien CR (Attachment H to Amendment A).

English language translation of published Chinese patent application Publication No. 1418631 (May 21, 2003).

English language translation of published Japanese patent application Publication No. 6-065103 (Mar. 8, 1994).

* cited by examiner

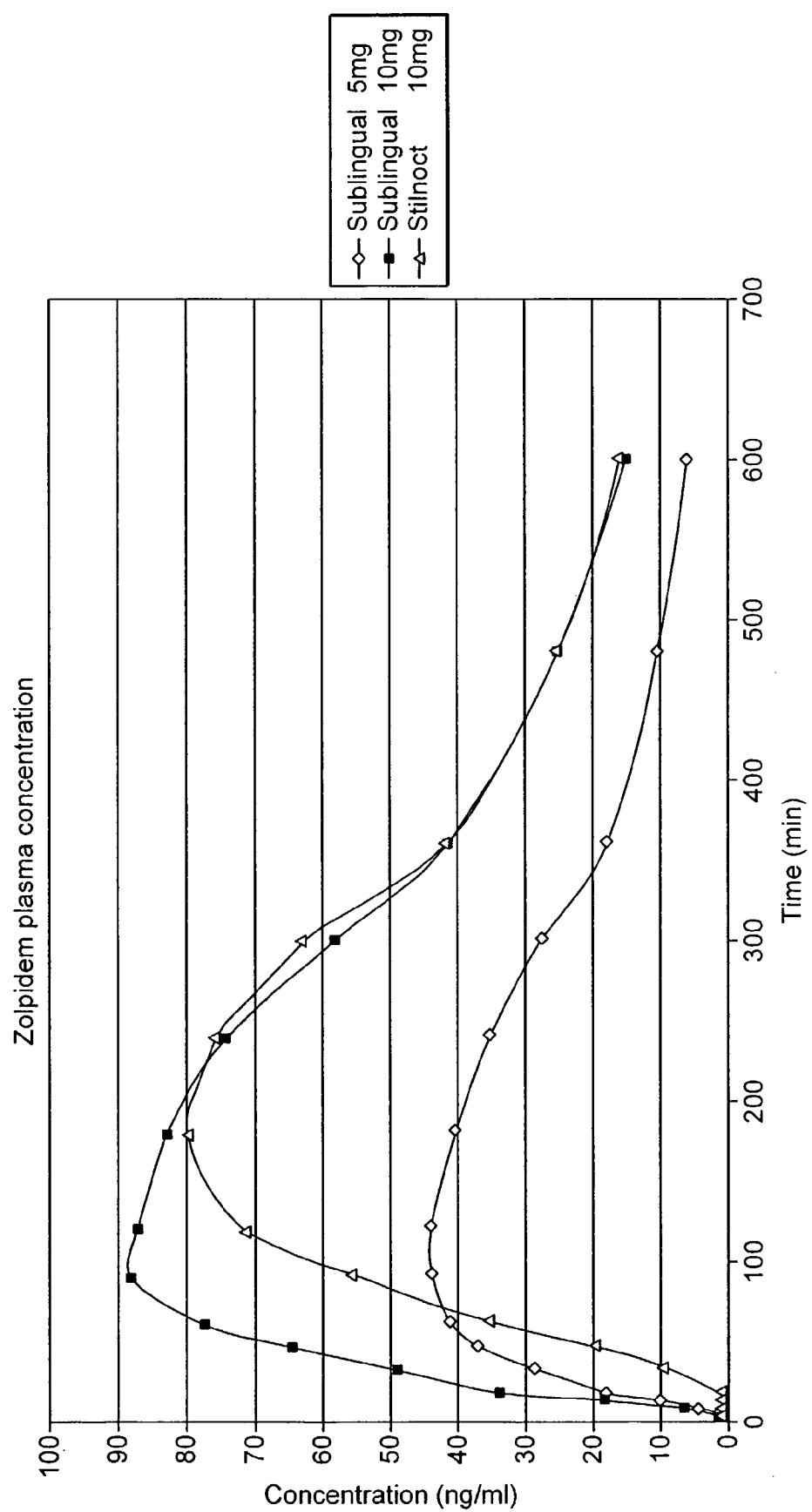

PHARMACEUTICAL FORMULATIONS USEFUL IN THE TREATMENT OF INSOMNIA

This invention relates to new, fast acting pharmaceutical formulations comprising short acting hypnotic agents that are useful in the short-term treatment of insomnia, such as transient insomnia.

Insomnia is a common disorder characterised by difficulty in the initiation and/or maintenance of sleep. Insomnia periodically affects 30% of adults. Furthermore, more than 90% of the total population have trouble with sleep at some point during their lives.

Inadequate sleep impairs quality of life and ability to function normally in a general sense. It often results in adverse personal, medical or psychiatric consequences, in addition to increasing the risk of accidents.

The disorder can be transient or chronic. Although isolated incidents of short-term insomnia may be caused by, for example, grief, stress, or short-term exposure to substances that are known to impair sleep, many patients who suffer from transient insomnia may experience the disorder regularly and/or periodically on a short-term basis.

In the treatment of short-term insomnia, consideration needs to be given to the potential side effects of the medicament employed, including any associated drug dependency. The practitioner also needs to be aware of the potential for undesirable absorption of drug taking place several hours after administration, which may give rise to decreased alertness and impaired psychomotor function during normal activity the following day. In this respect, wherever possible, it is important to expose patients only to short-term, or "on-demand", use of the lowest effective dose of any particular drug.

Zolpidem (N,N-dimethyl-2-(6-methyl-2-p-tolylimidazo[1,2-a]pyridin-3-yl)acetamide) is a short-acting sedative that is used in the short-term management of insomnia. The drug possesses a short half-life and produces no active metabolites. It appears to act by binding to the benzodiazepine receptor component of the GABA receptor complex and accordingly possesses similar properties to the benzodiazepines. However, zolpidem has the general advantage of minimal anxiolytic, myorelaxant and convulsant properties.

Currently-available zolpidem formulations comprise doses of between 5 and 10 mg of the drug in the form of its hemitartrate salt (see, for example, *British National Formulary*, Volume 48, pages 174 and 175). These compositions are administered orally, typically before retiring, and rapidly disintegrate in the gastrointestinal tract to provide for systemic absorption of drug.

Although zolpidem is rapidly absorbed from the gastrointestinal tract, its bioavailability is reported to be 70% following oral administration. Peak plasma concentrations are thereby typically reached within 1 and 5 hours of oral administration using current formulations.

In view of this, onset of action can be delayed in many patients, leading to a frustrating lack of "on demand" sleep, in addition, in many cases, to undesirable residual effects (such as those mentioned hereinbefore) the following day. Equally importantly, in view of the first-pass and/or pre-systemic metabolism that is typically connected with oral administration, the use of currently-marketed zolpidem formulations is characterised by considerable inter- and intra-individual variability in terms of both onset of action and residual effects (see, for example, Holm et al, *Drugs* (2000) 59, 865; Darcourt et al, *J. Pharmacol.*, (1999) 13, 81; Terzano et al, *Drug Safety* (2003) 26, 261; Salvà and Costa, *Clin. Pharmacokinet.* (1995) 29, 142; Drover et al, *Clin. Ther.* (2000) 22, 1443; and "*Guidance for Industry; Labelling Guidance for Zolpidem Tablets*", US Department of Health and Human Service (1997)).

Thus, there is a clear unmet clinical need for an improved formulation comprising a short acting hypnotic agent, such as zolpidem, which exhibits, in a consistent fashion, a more rapid, and preferably almost instantaneous, onset of action (e.g. within minutes rather than hours), as well as fewer residual effects the following day.

A biphasic peroral dosage form comprising zolpidem has recently been described in inter alia U.S. Pat. No. 6,514,531 B1. This system provides for an initial immediate release phase to induce sleep as rapidly as is possible with existing commercial formulations. This is followed by a controlled-release phase with the objective of maintaining sleep following induction. Other biphasic tablets comprising zolpidem are disclosed in European patent application EP 1 260 216 A1.

U.S. Pat. No. 6,638,535 B2 also discloses sustained release pellets comprising short acting hypnotic agents, such as zolpidem, zopiclone and zaleplon which provides for an in vitro release of less than 60% of active ingredient within the first 5 minutes of the in vitro test.

International patent application WO 00/16750 discloses a drug delivery system for the treatment of acute disorders by mucosal administration, in which the active ingredient is in microparticulate form and is adhered to the surface of larger carrier particles in the presence of a bioadhesion and/or mucoadhesion promoting agent.

International patent application WO 03/059349 discloses oral dosage forms comprising inter alia zolpidem, in addition to a solubility enhancer (e.g. a surfactant) and a spheronization agent (e.g. a distilled monoglyceride).

The skilled person would expect that transmucosal administration of an active ingredient across the pulmonary, nasal or oral mucosa (e.g. sublingual administration) would give rise to an enhanced rate of absorption of that active into plasma (as compared to an oral formulation), and thereby result in a vastly increased bioavailability at an early stage following administration. In the treatment of insomnia with a short acting hypnotic agent such as zolpidem, such an enhanced rate of absorption might be expected to give rise to potential safety problems in patients that are sensitive to the drug, potentially giving rise to undesirable pharmacological effects, such as a more rapid onset of sleep than is convenient (e.g. when preparing for sleep; see, for example col. 2, lines 9 to 18 of U.S. Pat. No. 6,638,535 B2). Moreover, the skilled person would also expect such a rapid absorption to compromise the duration of action of the relevant drug, and thereby the ability to maintain sleep during the night, especially given that short acting compounds are known to rapidly eliminated from plasma (see, for example, col. 2, lines 19 to 31 of U.S. Pat. No. 6,638,535 B2).

Surprisingly, we have found that safe and reliable "on demand" sleep induction (and maintenance) may be provided by way of a formulation as described hereinafter.

According to a first aspect of the invention, there is provided a pharmaceutical formulation suitable for transmucosal administration comprising a short acting hypnotic drug, which formulation provides a measurable plasma concentration of that drug within 10 minutes of administration.

The measurement of drug plasma concentration may be achieved by techniques that are well known in the art, for example as described hereinafter.

However, as a guide, we have found that formulations suitable for transmucosal administration are capable of providing a measurable plasma concentration of drug within 10 minutes of administration if, when measured in a standard in vitro dissolution (paddle) apparatus according to the United States Pharmacopoeia, using a phosphate buffer at pH 6.8 (USP) as dissolution medium, at least 50% of the active ingredient is released within 5 minutes, preferably within 4 minutes, for example within 3, or even 2, minutes. By the term "released" we mean that the active ingredient is released from the formulation and dissolved in the dissolution medium.

We have found that formulations according to the present invention are capable of providing first measurable plasma drug concentrations with a surprising degree of consistency, as expressed as the coefficient of variation (CV; a statistical measure of the deviation of a variable from its mean) for the time to first measurable plasma concentration. Observed CV values may be less than 50%, for example less than 40% for this variable.

Thus, as formulations according to the present invention consistently provide measurable plasma concentrations of drug within 10 minutes they are effectively capable of providing for consistent "on demand" sleep induction.

According to a further aspect of the invention, there is provided a transmucosal formulation suitable for providing sleep on demand, which formulation comprises a short acting hypnotic drug.

By "sleep on demand", we include that the formulation consistently induces sleep, i.e. in at least 90% of cases (on an intra- and/or inter-patient basis), within 60 minutes, preferably within 45 minutes, more preferably within 30 minutes and especially within 20 (e.g. 15) minutes.

We have also found, very surprisingly, that formulations according to the present invention are capable of providing rates of absorption of drug following administration that are not substantially different to those that are observed in currently-available oral formulations. In view of this, formulations according to the present invention are capable of reducing or preventing inconveniently rapid onset of sleep, or other undesirable pharmacological effects that might be associated with rapid absorption, for example, in patients that are particularly sensitive to the relevant drug, as discussed hereinbefore.

In this respect, there is also provided a transmucosal formulation suitable for providing sleep on demand, which formulation comprises a short acting hypnotic drug, wherein the formulation provides for a time difference between:

(a) the first measurable; and
(b) the maximum measured plasma concentration of drug following administration of the formulation, which time difference is within the range of about 50 minutes to about 250 minutes, preferably about 55 minutes to about 230 minutes, more preferably about 70 minutes to about 180 minutes and particularly about 80 to about 160 minutes.

Equally surprisingly, we have also found that formulations according to the present invention are capable of providing levels of drug at an appropriate time after administration and following sleep induction that are not substantially different to those that are observed in currently-available oral formulations. In view of this, formulations according to the present invention are capable of maintaining a drug-induced sleep throughout the night.

In this respect, there is also provided a transmucosal formulation suitable for providing sleep on demand, which formulation comprises a short acting hypnotic drug, wherein the formulation provides for a plasma concentration of drug that is capable of maintaining sleep at least about 3 hours after administration of the formulation, preferably at least about 4 hours, more preferably at least about 5 hours and particularly at least about 6 hours, after administration. In otherwise healthy adult patients below the age of 60, plasma concentrations of drug that are capable of maintaining sleep are for example in the range of about 40 to about 100 ng/mL of plasma, for example about 50 to about 90 ng/mL, such as about 60 to about 85 ng/mL.

Furthermore, formulations according to the present invention are capable of providing levels of drug at an appropriate time after administration that do not give rise to the undesirable residual effects mentioned hereinbefore the following day.

In this respect, there is also provided a transmucosal formulation suitable for providing sleep on demand, which formulation comprises a short acting hypnotic drug, wherein the formulation provides for a plasma concentration of drug that that does not result in decreased alertness and/or impairment of psychomotor function in a patient following sleep at least about 8 hours, such as about 7 hours after administration. In otherwise healthy adult patients below the age of 60, plasma concentrations of drug that are not capable of producing such effects, which effects may be objective (i.e. measurable by some test or marker) or subjective (i.e. the subject gives an indication of, or feels, such effects), are, for example, less than about 40 ng/mL of plasma, for example less than about 30 ng/mL, such as less than about 25 ng/mL.

It will be appreciated by the skilled person that the aforementioned plasma concentration ranges of active ingredient are exemplary of the average case and are likely to vary with the severity of the insomnia that is to be treated, as well as the age, weight, sex, renal function, hepatic function and response of the particular patient to be treated. There can, of course, be individual instances where plasma concentrations that are outside the ranges specified above may give rise to the stated effects, and such are within the scope of this invention. For example, for children or elderly patients, the aforementioned plasma concentration ranges may be approximately halved in order to produce (or not produce) the relevant effect.

Transmucosal drug delivery may be provided over the pulmonary, the nasal or, more preferably, the oral, mucosa. Pulmonary transmucosal drug delivery may be provided, for example, by way of a inhaler comprising a powder formulation that includes the active ingredient. Nasal transmucosal drug delivery may be provided, for example, by way of a nasal spray comprising a powder formulation that includes the active ingredient. Oral transmucosal delivery may be provided, for example, by way of a spray comprising a powder formulation that includes the active ingredient for spraying, for example, under the tongue, or by way of effervescent formulations or freeze-dried rapid melting tablet formulations, all of which are known to those skilled in the art.

However, we prefer that formulations according to the present invention are in the form of sublingual tablets. Sublingual tablets that provide for sleep on demand may be prepared as described hereinafter.

According to a further aspect of the invention there is provided a sublingual tablet formulation that is suitable for providing sleep on demand, which formulation comprises particles of:

(a) a short acting hypnotic drug; and
(b) a mucoadhesion promoting agent, which particles of components (a) and (b) are each presented, at least in part, upon the surfaces of larger carrier particles.

It will be clear to the skilled person that formulations according to the present invention will comprise a pharmacologically effective amount of short acting hypnotic drug (i.e. the "active" ingredient of the formulation). The term "pharmacologically effective amount" refers to an amount of active ingredient, which is capable of conferring the desired therapeutic effect on a treated patient, whether administered alone or in combination with another active ingredient. Such an effect may be objective (i.e. measurable by some test or marker) or subjective (i.e. the subject gives an indication of, or feels, an effect).

Short acting hypnotic drugs that may be employed in formulations according to the present invention include zopiclone, zaleplon, indeplon or, preferably, zolpidem, and pharmaceutically acceptable salts of all of these. Also included are diastereomeric (e.g. enantiomeric) forms, as well as active metabolites, of these compounds/salts.

Preferred salts of zolpidem that may be employed include hydrochloride salts, methanesulphonate salts, tosylate salts, fumarate salts, sulphate salts and tartrate salts, such as the hydrogen tartrate or the hemitartrate salt.

The active ingredient is preferably presented in the form of microparticles, preferably with a weight based mean diameter of between about 0.5 µm and about 15 µm, such as about 1 µm and about 10 µm. The term "weight based mean diameter" will be understood by the skilled person to include that the average particle size is characterised and defined from a particle size distribution by weight, i.e. a distribution where the existing fraction (relative amount) in each size class is defined as the weight fraction, as obtained e.g. by sieving.

Microparticles of active ingredients may be prepared by standard techniques, such as grinding, dry milling, wet milling, precipitation, micronisation, etc.

The amount of active ingredient that may be employed in a sublingual tablet may be determined by the physician, or the skilled person, in relation to what will be most suitable for an individual patient. This is likely to vary with the severity of the condition that is to be treated, as well as the age, weight, sex, renal function, hepatic function and response of the particular patient to be treated.

Suitable quantities of active ingredient that may be employed in tablet formulations may be in the range 2 to 20% by weight based upon the total weight of the formulation. More preferably, formulations may contain between 4 and 17% by weight of active ingredient, and especially from about 5 to about 15%. The amount of active ingredient may also be expressed as the absolute amount in a tablet formulation. In such a case, the total amount of active ingredient that may be present may be sufficient to provide a dose of drug per tablet that is in the range 3 to 15 mg, such as 4 to 13 mg and in particular between about 5 and about 12 mg.

The above-mentioned dosages are exemplary of the average case; there can, of course, be individual instances where higher or lower dosage ranges are merited, and such are within the scope of this invention.

Tablet formulations described herein comprise one or more mucoadhesion promoting agent and may thus facilitate the partial or complete adhesion of active ingredients to a biological surface, such as a mucosal membrane.

In the context of the present invention, the terms "mucoadhesive" and "mucoadhesion" refer to adhesion or adherence of a substance to a mucous membrane within the body. The skilled person will appreciate that the expressions "mucoadhesion" and "bioadhesion" may often be used interchangeably. In this respect, the presence of a mucoadhesion promoting agent helps facilitate the partial or complete adhesion of sublingual tablets comprising active ingredient to the mucosal membrane under the tongue.

A variety of substances known in the art can be used as mucoadhesion promoting agents, for example polymeric substances, preferably with an average (weight average) molecular weight above 5,000. It is preferred that such materials are capable of rapid swelling when placed in contact with water and/or, more preferably, mucous, and/or are substantially insoluble in water at room temperature and atmospheric pressure.

Examples of suitable mucoadhesion promoting agents include cellulose derivatives such as modified cellulose gum and, more particularly, hydroxypropylmethyl cellulose (HPMC), hydroxyethyl cellulose (HEC), hydroxypropyl cellulose (HPC), methyl cellulose, ethyl hydroxyethyl cellulose, carboxymethyl cellulose and sodium carboxymethyl cellulose (NaCMC); starch derivatives such as modified starch, sodium starch glycolate and, more particularly, moderately cross-linked starch; acrylic polymers such as carbomer and its derivatives (Polycarbophyl, Carbopol®, etc.); polyvinylpyrrolidone; polyethylene oxide (PEO); chitosan (poly-(D-glucosamine)); natural polymers such as gelatin, sodium alginate, pectin; scleroglucan; xanthan gum; guar gum; poly co-(methylvinyl ether/maleic anhydride); and crosscarmellose (e.g. crosscarmellose sodium). Such polymers may be crosslinked. Combinations of two or more bio/mucoadhesive polymers can also be used.

Suitable commercial sources for representative bio/mucoadhesive polymers include: Carbopol® acrylic copolymer (BF Goodrich Chemical Co, Cleveland, 08, USA); HPMC (Dow Chemical Co., Midland, Mich., USA); NEC (Natrosol; Hercules Inc., Wilmington, Del. USA); HPC (Klucel®; Dow Chemical Co., Midland, Mich., USA); NaCMC (Hercules Inc. Wilmington, Del. USA); PEO (Aldrich Chemicals, USA); sodium alginate (Edward Mandell Co., Inc., Carmel, N.Y., USA); pectin (BF Goodrich Chemical Co., Cleveland, Ohio, USA); crosslinked polyvinylpyrrolidone (Kollidon CL®, BASF, Germany, Polyplasdone XL®, Polyplasdone XL-10® and Polyplasdone INF-10®, ISP Corp., US); Ac-Di-Sol® (modified cellulose gum with a high swellability; FMC Corp., USA); Actigum (Mero-Rousselot-Satia, Baupte, France); Satiaxana (Sanofi BioIndustries, Paris, France); Gantrez® (ISP, Milan, Italy); chitosan (Sigma, St Louis, Mo., USA); and sodium starch glycolate (Primojel®, DMV International BV, Netherlands, Vivastar®, J. Rettenmaier & Söhne GmbH & Co., Germany, Explotab®, Roquette America, US).

However, preferred mucoadhesion promoting agents that may be employed in sublingual tablet formulations described herein include sodium carboxymethylcellulose.

Suitable forms of sodium carboxymethylcellulose include internally crosslinked sodium carboxymethylcellulose, such as croscarmellose sodium NF (e.g. Ac-Di-Sol® (FMC Corp., USA)).

Suitably, the amount of mucoadhesion promoting agent that is present in a tablet formulation may be in the range 0.1 to 25%, such as 0.5 to 15% and preferably 1 to 10% by weight based upon the total weight of the formulation. A preferred range is from 2 to 8%, such as from about 3.5 to about 6.5% (e.g. about 5%) by weight.

Tablet formulations described herein may comprise one or more binder and/or disintegrating agent or "disintegrant". A binder may be defined as any material that is capable of acting as a bond formation enhancer, facilitating the compression of the powder mass into coherent compacts.

A disintegrant may be defined as any material that is capable of accelerating to a measurable degree the disintegration/dispersion of a tablet formulation, and in particular carrier particles, as defined herein. This may be achieved, for example, by the material being capable of swelling and/or expanding when placed in contact with water and/or mucous (e.g. saliva), thus causing the tablet formulations/carrier particles to disintegrate when so wetted.

Suitable disintegrants include cross-linked polyvinylpyrrolidone, carboxymethyl starch and natural starch, and suitable binders include cellulose gum and, particularly, microcrystalline cellulose.

Preferred forms of microcrystalline cellulose include silicified microcrystalline cellulose (a mixture of microcrystalline cellulose and a small amount of colloidal silicon dioxide), such as ProSolv® (JRS Pharma, Germany).

If present, binders and/or disintegrating agents are preferably employed in an amount of between 0.5 and 10% by weight based upon the total weight of the formulation. A preferred range is from 1 to 8% (e.g. 5%), such as from about 2.0 to about 3.0% (e.g. about 2.25%) by weight.

It should be noted that sodium carboxymethylcellulose may function in tablet formulations described herein both as a mucoadhesion promoting agent and as a disintegrating agent.

Preferably, carrier particles for use in tablet formulations described herein are of a size that is between about 50 and about 750 μm, and preferably between about 100 and about 600 μm, such as between about 150 μm and about 400 μm (e.g. about 200 μm). Suitable carrier particle materials include carbohydrates, e.g. sugar, mannitol and lactose; pharmaceutically-acceptable inorganic salts, such as sodium chloride, calcium phosphate, dicalcium phosphate hydrate, dicalcium phosphate dehydrate, tricalcium phosphate, calcium carbonate, and barium sulfate; polymers, such as microcrystalline cellulose, cellulose and crosslinked polyvinylpyrrolidone; or mixtures thereof. It is preferred that the carrier particle material comprises a pharmaceutically-acceptable substance that is adequately soluble in water (e.g. exhibits a solubility of greater than 0.01 g/mL at room temperature and atmospheric pressure). Preferred materials thus include sugar alcohols and/or sugars, such as mannitol and lactose, or pharmaceutically-acceptable inorganic salts, such as sodium chloride.

Preferred carrier particle materials include mannitol, such as granulated mannitol (Pearlitol 400 DC; Roquette, France) and spray-dried mannitol (Parteck M200; Merck, Germany).

Carrier particles preferably comprise an amount of between 50 and 95% by weight based upon the total weight of the formulation. A preferred range is from 60 to 90%, such as from 65 to 85% (e.g. between about 70 and about 85%) by weight.

It is preferred that the relative sizes and amounts of the particles of active ingredient and the carrier particles that are employed are sufficient to ensure that the carrier particles may be at least about 90% covered by the active ingredient, for example at least about 100% and up to about 200% (e.g. between about 130% and about 180%) covered. The skilled person will appreciate in this context that "100% coverage" of the carrier particles by the active ingredient means that the relative particle sizes and amounts of the relevant particles that are employed are sufficient to ensure that the entire surface area of each carrier particle could be covered by the particles of the active ingredient notwithstanding that other ingredients (e.g. mucoadhesion promoting agent) may also be present in a tablet formulation. Obviously, if other such ingredients are employed, then the actual degree of coverage of carrier particles by active ingredient may be less than the amounts specified above. 200% coverage means that there is sufficient particles of active ingredient to cover the surfaces of the carrier particles twice over, notwithstanding the presence of other ingredients.

It is surprising that such tablet formulations with greater than 90% theoretical coverage are effective. Based on current knowledge, the skilled person would understand that, in order to ensure rapid dissolution, it would be important to ensure that the relative sizes/amounts of active ingredient/carrier particles are sufficient to ensure that 70% or less of the surfaces of the latter could be covered by the former.

Tablet formulations may be prepared by standard techniques, using standard equipment known to the skilled person.

Active ingredient and other essential constituents mentioned hereinbefore may be combined with conventional pharmaceutical additives and/or excipients used in the art for such preparations, and thereafter preferably directly compressed/compacted into tablets. (See, for example, *Pharmaceutical Dosage Forms: Tablets. Volume* 1, $2^{nd}$ Edition, Lieberman et al (eds.), Marcel Dekker, New York and Basel (1989) p. 354-356 and the documents cited therein.)

Suitable further additives and/or excipients may thus comprise:

(a) surfactants or wetting agents, which may enhance that hydration of the active ingredient and carrier particles, resulting in faster initiation of both mucoadhesion and dissolution. If present, the surfactant should be provided in finely dispersed form and mixed intimately with the active ingredients. Examples of suitable surfactants include sodium lauryl sulphate, polysorbates, bile acid salts and mixtures thereof. If present, the surfactant may comprise between 0.3 and 5% by weight based upon the total weight of the tablet formulation, and preferably between 0.5 and 3% by weight;

(b) lubricants (such as sodium stearyl fumarate or, preferably, magnesium stearate). When a lubricant is employed it should be used in very small amounts (e.g. up to about 3%, and preferably up to 2%, by weight based upon the total weight of the tablet formulation);

(c) flavourings (e.g. lemon, menthol or, preferably, peppermint powder), sweeteners (e.g. neohesperidin) and dyestuffs; and/or (d) other ingredients, such as carrier agents, preservatives and gliding agents.

The various ingredients may be dry mixed together in several ways for a sufficient time in order to produce a mixture. This results in discrete particles of drug and other relevant excipients, in particular the mucoadhesion promoting agent, being presented on, and/or adhered to, the surfaces of the carrier particles. Standard mixing equipment may be used in this regard. The mixing time period is likely to vary according to the equipment used.

Suitable compacting equipment includes standard tabletting machines, such as the Kilian SP300 or the Korsch EK0.

Irrespective of the foregoing, the tablet formulation should be essentially free (e.g. less than 20% by weight based on the total weight of the formulation) of water. It will be evident to the skilled person that "premature" hydration will dramatically decrease the mucoadhesion promoting properties of a tablet formulation and may result in premature dissolution of the active ingredient.

Suitable final sublingual tablet weights are in the range 30 to 400 mg, such as 50 to 200 mg, for example 60 to 180 mg, more preferably between about 70 and about 160 mg. Suitable final tablet diameters are in the range 4 to 10 mm, for example 5 to 9 mm, and more preferably about 6 to about 8 mm. A preferred tablet weight is about 80 mg and a preferred tablet diameter is about 6 mm.

Wherever the word "about" is employed herein in the context of concentrations (e.g. of drug in plasma), timescales (e.g. in vitro drug release and measured/measurable drug plasma concentrations), dimensions (e.g. particle and tablet sizes), surface coverage (e.g. of carrier particles by active ingredient), and amounts (e.g. absolute doses of active ingredient and relative amounts of individual constituents), it will be appreciated that such variables are approximate and as such may vary by ±10%, e.g. ±5%, from the numbers specified herein.

The tablet formulations described herein may be administered sublingually by way of appropriate dosing means known to the skilled person. A sublingual tablet may be placed under the tongue, and the active ingredients absorbed through the surrounding mucous membrane.

The formulations according to the present invention are useful in the treatment of insomnia and particularly transient insomnia. According to a further aspect of the invention there is provided a method of treatment of insomnia which method comprises administration of a formulation according to the invention to a person suffering from, or susceptible to, such a condition.

For the avoidance of doubt, by "treatment" we include the therapeutic treatment, as well as the symptomatic treatment, the prophylaxis, or the diagnosis, of a condition.

The formulations according to the present invention are easy and inexpensive to manufacture, and consistently enable the rapid uptake of the active ingredient through the mucosa, such as the oral mucosa. This enables "on demand" sleep, which is achievable before retiring, following an interruption of sleep, or in other situations when rapid sleep induction is desired. Most usefully, formulations according to the present invention are capable of providing this effect, whilst at the same time reducing or preventing inconveniently rapid onset of sleep in, for example, patients that are particularly sensitive to the relevant drug.

Furthermore, formulations according to the present invention are capable of maintaining a drug-induced sleep throughout the night, whilst at the same time preventing or reducing the post-sleep residual effects mentioned hereinbefore.

Finally, the present invention enables these surprising effects to be achieved in a highly consistent manner, in which inter- and intra-individual variations are significantly reduced or eliminated, providing the physician and end user with a dosage form that is capable of providing far more reliable sleep, both in terms of induction and duration.

Formulations according to the present invention may also have the advantage that they may be prepared using established pharmaceutical processing methods and employ materials that are approved for use in foods or pharmaceuticals or of like regulatory status.

Formulations according to the present invention may also have the advantage that they may be more efficacious than, be less toxic than, be more potent than, produce fewer side effects than, be more easily absorbed than, and/or have a better pharmacokinetic profile than, and/or have other useful pharmacological, physical, or chemical properties over, pharmaceutical formulations known in the prior art, whether for use in the treatment of insomnia or otherwise.

The invention is illustrated by way of the following examples with reference to FIG. 1, which shows a comparison of plasma concentrations of zolpidem produced by way of two sublingual tablet formulations according to the present invention versus a commercially-available peroral formulation.

EXAMPLE 1

Preparation of Sublingual Tablets

Sublingual tablets comprising 5 mg and 10 mg of zolpidem hemitartrate were prepared as follows.

Zolpidem hemitartrate (Boehringer Ingelheim, Germany) was firstly ground for 20 minutes in a ball mill.

The active ingredient was then accurately weighed out, along with the other excipients (see below), in appropriate proportions that would enable the production of tablets with the absolute amounts of various ingredients mentioned below.

Pre-weighed quantities of zolpidem hemitartrate and mannitol (Parteck M200; Merck, Germany) were then mixed in a Turbula mixer for 96 hours. Then, pre-weighed quantities of silicified microcrystalline cellulose (ProSolv®; JRS Pharma, Germany), sodium carboxymethylcellulose (Croscarmellose Sodium NF; Ac-Di-Sol®; FMC Corp., USA), Neohesperidin DC (Exquim, Spain) and peppermint powder (Firmenich, Germany) were added and mixing was continued for 30 minutes. Finally, a pre-weighed quantity of magnesium stearate (Peter Greven, Netherlands) was added and mixing continued for another 2 minutes.

The powder mixture was then compacted using a single punch press (Korsch EK0) with 6 mm flat bevel edged punches, to produce tablets of a total weight of 80 mg.

The absolute amounts of individual ingredients are as presented in the table below.

In-process controls were employed (tablet weight, crushing strength, friability and disintegration time), with test samples being withdrawn throughout the tabletting process. Tablets were packaged and labelled for use in Example 2.

| Ingredient | 5 mg Tablet Amount (mg) | 10 mg Tablet Amount (mg) |
| --- | --- | --- |
| zolpidem hemitartrate | 5.00 | 10.00 |
| mannitol | 65.00 | 60.00 |
| silicified microcrystalline cellulose | 1.80 | 1.80 |
| sodium carboxymethylcellulose | 4.00 | 4.00 |
| neohesperidin | 0.20 | 0.20 |
| peppermint powder | 3.00 | 3.00 |
| magnesium stearate | 1.00 | 1.00 |
| Total tablet weight | 80.00 | 80.00 |

EXAMPLE 2

Clinical Study

An open randomized three-period crossover single-centre study was devised to evaluate the pharmacokinetic profile of the sublingual zolpidem 5 mg and 10 mg tablets prepared by way of Example 1 above, as compared to a peroral zolpidem formulation (Stilnoct® 10 mg; Sanofi-Synthélabo, France).

The trial was a pharmacokinetic study in healthy male and female volunteers to test for dose proportionality as between the two sublingual tablet formulations. The pharmacokinetic profiles were evaluated, focussing on bioavailability and time and rate of absorption. The study also included a subjective assessment of efficacy, i.e. the subjects' perceived degree of sedation.

18 healthy subjects aged between 18 and 40 were used in this study. Signed informed consents were obtained in all cases.

Each of the three formulations were given to each of the 18 volunteers, in a random order, at three visits to the study centre (hereinafter "Visits 1, 2 and 3"). Visits 1 and 2 were followed by a wash-out period of at least 2 days.

At a pre-study visit, the subjects underwent a full clinical examination to assess medical history, undertake a physical examination, with routine screens for haematology, clinical chemistry, drugs and alcohol. This pre-study visit was conducted no more than 14 days prior to Visit 1.

Blood samples for determination of the concentration of zolpidem in plasma were collected on 14 occasions on each study day. Samples were collected immediately before administration and at 5, 10, 15, 30, 45, 60, 90, 120, 180, 240, 300, 360, 480 and 600 minute intervals thereafter. Tolerability and safety parameters were followed during the study day. Subject-rated sedation scores by visual analogue scales were assessed during each study day.

A safety follow-up visit, which included a physical examination, with routine screens for haematology and clinical chemistry was performed no more that 10 days after Visit 3.

Any of the following was regarded as a criterion for exclusion from the study:
1. the subject was overweight (i.e. with a body mass index of greater than 30);
2. the subject was a smoker;
3. if the subject had drank alcohol within the previous 24 hours;
4. if the subject showed any evidence of drug abuse;
5. if the subject had used a prescription medication within the previous 14 days;
6. if, in the investigator's judgement, the subject exhibited clinically significant abnormalities at the screening examination or in the laboratory test results; and
7. if the subject was female and was either pregnant, breast feeding or was of childbearing potential and was not using adequate birth control.

Subjects were free to discontinue their participation in the study at any time. A subject could be withdrawn from the study at any time at the discretion of the investigator. Subjects were to be discontinued from the study in event of, for example:
1. unacceptable adverse events;
2. non-compliance with the study protocol; or
3. failure to attend study visits.
However, all subjects completed the study in accordance with the protocol and none of the subjects were replaced.

Each subject received three single doses of each of the three formulations. The study nurse made sure that the formulations were administered correctly, with the sublingual tablets administered deeply under the tongue with the subject remaining in a supine position for at least ten minutes. The oral tablet was swallowed.

Confirmed eligible subjects were assigned a subject number in a strictly consecutive order. Each subject number was randomised to one of six possible treatment sequences (3×2×1) according to a computer generated randomisation list provided by the study statistician. Three subjects were thus assigned to each treatment sequence.

In order to allow time for 10 hours of blood plasma sampling, administration of the study drug formulation took place at approximately 0800 hours on the morning of each visit.

The subjects fasted overnight before each visit. Upon arrival at the clinic, the subjects had a standard breakfast, after which study drug was administered. Standard meals were served during the study day, with lunch at 1200 hours and dinner at 1700 hours. Subjects had their meals after taking blood samples at 240 minutes and 480 minutes, and never directly before blood sampling.

Blood samples (7 mL) were collected in heparinised Vacutainer® tubes. The samples were kept on ice and then centrifuged for 10 minutes at 2000×g. The plasma was transferred into labelled plastic tubes and stored at −20° C. prior to analysis. The frozen plasma samples were transported to Quintiles, Uppsala, Sweden, where the zolpidem concentration in the samples was measured.

Pharmacokinetic variables were derived from the zolpidem plasma concentration time curve. The primary pharmacokinetic variable was $AUC_{0-t}$, i.e. the area under the zolpidem plasma concentration time curve from 0 minutes to 600 minutes after administration of study drug.

To further evaluate the pharmacokinetic profile of the sublingual zolpidem formulations, the following secondary pharmacokinetic variables were derived from the plasma concentration time curve:
(a) the area under the curve from 0 minutes extrapolated to infinity ($AUC_{0-\infty}$);
(b) maximum plasma concentration ($C_{max}$);
(c) time for maximum plasma concentration ($t_{max}$);
(d) half-life of the active substance ($t_{1/2}$);
(e) first measurable plasma concentration ($C_{first}$); and
(f) time to first measurable plasma concentration ($t_{first}$).

The primary efficacy variable was subject-rated sedation as measured on a VAS. The VAS consisted of a 100 mm non-graded scale between the extremes "completely awake" and "practically asleep". The subjects were to fill in the sedation scales immediately before administration of study drug and at 30, 60, 90, 120, 150, 180, 210, 240, 270, 300, 330, 360, 390, 420, 450, 480, 510, 540, 570 and 600 minutes afterwards. If the subject fell asleep, the study nurse made a note of this in the case report form.

Safety variables included adverse events reported and laboratory assessments.

The recording of adverse events was made on each study visit and on the post-study visit. Patients were also free to report adverse events between visits. Adverse events were to be registered by the reporting of spontaneously mentioned symptoms and by open questioning. The investigator and the medical/laboratory staff were also instructed to record any adverse event that they observed during the investigation.

Plasma concentrations of zolpidem were determined by using HPLC with fluorescence detection. This analytical procedure is capable of measuring concentrations of zolpidem in human plasma within the range 1.0 to 400 ng/mL. Zolpidem and an internal standard Trazodone were purified from human heparin plasma by solid phase extraction using Bond Elute $C_{18}$ cartridges, rinsed with water and eluted with methanol. The eluate was injected onto a reversed phase $C_{18}$ LC column (150×4.6 mm, 5 µm) with a mobile phase composed of acetonitrile:50 mM potassium phosphate buffer at pH 6.0 (4:6, v/v) and determined by fluorescence detection (excitation at 254 nm and emission at 400 nm).

The study was performed in accordance with Good Clinical Practise (GCP) and Good Laboratory Practise (GLP). In order to ensure the use of standard terminology, and the collection of accurate, consistent, complete and reliable data, the study was preceded by a training session for the investigator and study nurses.

The study was regularly monitored by external monitors appointed by the study sponsor. Complete source data verification of all parameters was performed and the case report forms were thereafter collected from the study site. Data was checked for accuracy by proof-reading, entered into a database, validated and analysed by the sponsor. All corrections and additions were signed and dated by the investigator.

Log AUC and log dose adjusted AUC were analysed using the SAS statistical program PROC GLM (SAS Institute Inc., Cary, N.C., USA) with subject, treatment and period as class variables. Differences between treatments were given as 90% confidence intervals. Equivalence, and dose proportionality, respectively, were considered proven if the 90% confidence interval for the difference between treatments/doses did not exceed ±20% (or the ratio was within 0.80 and 1.25).

The quality of the determination of zolpidem concentration was satisfactory and within the quality control (QC) acceptance criteria of ±15%. The lower limit of quantification was 1.00 ng/ml for zolpidem in human plasma. The mean accuracy of the assay as determined from the analysis of QC samples was within ±10.0%.

Results

Pharmacokinetic data for all subjects are given as mean values in Table 1.

TABLE 1

Non-compartmental pharmacokinetic parameters (mean and SD) of zolpidem following sublingual and oral administration (n = 18).

| PK Parameter | 5 mg sublingual | 10 mg sublingual | Stilnoct ® |
|---|---|---|---|
| $AUC_{0-t}$ (min · ng/ml) | 14913.8 (SD 6714.2) | 30855.5 (SD 14446.7) | 26879.1 (SD 14605.3) |
| $AUC_{0-\infty}$ (min · ng/ml) | 16064.3 (SD 7770.4) | 33466.2 (SD 16682.5) | 30093.7 (SD 18976.9) |
| $C_{first}$ (ng/ml) | 5.2 (SD 2.8) | 8.7 (SD 5.8) | 10.8 (SD 11.5) |
| $t_{first}$ (min) | 6.4 (SD 2.3) | 6.4 (SD 2.3) | 47.5 (SD 34.6) |
| $C_{max}$ (ng/ml) | 50.0 (SD 20.8) | 98.8 (SD 32.7) | 90.6 (SD 35.1) |
| $t_{max}$ (min) | 92.5 (SD 42.8) | 122.5 (SD 58.3) | 176.7 (SD 79.6) |
| $t_{1/2}$ (h) | 2.57 (SD 0.79) | 2.56 (SD 0.82) | 2.58 (SD 1.04) |

These results demonstrate bioequivalence between the 10 mg sublingual tablet and Stilnoct® (10 mg) for $AUC_{0-t}$. Dose proportionality between sublingual zolpidem 5 mg and 10 mg tablets for dose adjusted $AUC_{0-t}$ was established.

Most surprisingly, the time to the first measurable plasma concentration ($t_{first}$) and the time to the maximum plasma concentration ($t_{max}$) are significantly shorter for the 10 mg sublingual tablet, as compared to Stilnoct® (p<0.0001 and 0.0165, respectively). See also FIG. 1 in this regard. The difference in the slope of the absorption curves i.e. absorption rate, is not statistically significant (p=0.478). Mean absorption rates are given in Table 2.

TABLE 2

Absorption rate (slope of absorption phase of concentration-time curve) by treatment, mean (SD) (n = 18).

| 5 mg sublingual | 10 mg sublingual | Stilnoct ® (10 mg) |
|---|---|---|
| 0.0344 (0.0108) | 0.0359 (0.0135) | 0.0315 (0.0206) |

The elimination half-life ($t_{1/2}$) of zolpidem was similar for the two sublingual tablets (2.57 and 2.56 hours, respectively), indicating that the elimination kinetics are linear. There was also no statistically significant difference in $t_{1/2}$ between the two sublingual tablets and Stilnoct® (2.58 hours). Elimination rates are given in Table 3.

TABLE 3

Elimination rate (slope of elimination phase of concentration-time curve) by treatment, mean (SD) (n = 18).

| 5 mg sublingual | 10 mg sublingual | Stilnoct ® (10 mg) |
|---|---|---|
| −0.0050 (0.0014) | −0.0052 (0.0021) | −0.0052 (0.0019) |

Subject-rated sedation VAS scores were assessed and compared between treatments. No significant differences in efficacy between treatments was found. However, after adjustment for period baseline VAS values (change from baseline) there was a statistically significant difference in mean VAS change from baseline between the sublingual 10 mg tablet and Stilnoct® in favour of the former (p=0.0062).

The number of subjects asleep was observed during ten hours following administration of the study drug. With the sublingual 10 mg tablet, more subjects were asleep at 90 minutes than for Stilnoct®.

To further assess and compare sleep after the different study drug administrations, the following values were calculated:

(a) first time of sleep (i.e. sleep latency; mean per treatment);
(b) total number of sleep episodes (i.e. the total number of 30 minute episodes any subject was asleep per treatment; there were 377 episodes altogether); and
(c) total sleeping time (mean per treatment).

TABLE 4

Additional sleep variables (n = 18)

| Sleep variable | 5 mg sublingual | 10 mg sublingual | Stilnoct ® 10 mg |
|---|---|---|---|
| First time of sleep (mean min) | 100.6 (39.6) | 85.0 (31.3) | 95.6 (38.3) |
| Total number of sleep episodes (n/377 and %) | 81/377 (21.5%) | 101/377 (26.8%) | 101/377 (26.8%) |
| Total sleep time (mean min) | 135.0 (70.7) | 168.3 (74.3) | 168.3 (98.8) |

For the sublingual 10 mg tablet and Stilnoct®, the total sleeping time as well as the number of sleeping episodes were similar, indicating that subjects slept equally long and deeply after administration of the two study drugs. The first time of sleep, however, occurred earlier for the sublingual 10 mg tablet, indicating that the onset of hypnotic effect is earlier for sublingual zolpidem compared to the oral administration (see Table 4).

In terms of safety, there were no unexpected or serious adverse events for any of the study medications.

CONCLUSIONS

This study shows that sublingual zolpidem (10 mg) tablets are bioequivalent to a peroral zolpidem formulation (Stilnoct®; 10 mg), with regard to $AUC_{0-t}$, $AUC_{0-inf}$ and $C_{max}$. The pharmacokinetic analysis further shows that the extent of absorption and bioavailability of zolpidem was linear throughout the studied dose interval. In addition, the initial absorption rate of sublingual zolpidem is unaffected by the dose, which indicates that the same time to onset of effect can be expected for both doses.

There were no statistically significant differences between doses for dose adjusted AUC and $C_{max}$, and dose proportionality of sublingual zolpidem 5 mg and 10 mg was established. The linear increase of the AUC with increased dose provides strong evidence for a similar extent of absorption of zolpidem after sublingual administration of the studied doses in these subjects.

Dose proportionality of sublingual zolpidem (5 mg and 10 mg tablets) was established, with $t_{first}$ and $t_{max}$ being significantly shorter for sublingual zolpidem. This demonstrated that an earlier absorption into the blood stream is achieved compared to oral administration. There is no statistically significant difference in the rate of absorption for sublingual zolpidem and Stilnoct® 10 mg, assessed from the slope of the absorption phase of the plasma time-concentration curves.

The lower inter- and intra-individual variability in the pharmacokinetic parameters of sublingual zolpidem versus oral zolpidem in healthy volunteers, suggest that the in vivo performance of the sublingual tablet is better.

There was a greater number of subjects falling asleep earlier after administration with sublingual 10 mg tablets, compared to the other study treatments. The mean total sleeping time, as well as the number of sleeping episodes was similar after treatment with sublingual 10 mg tablets and Stilnoct®.

These results indicate that formulations according to the present invention may be capable of providing, in a consistent fashion, sleep on demand in insomnia patients.

The invention claimed is:

1. A method of treating insomnia in an individual by sublingual administration of a pharmaceutical composition, the method comprising:
   providing the pharmaceutical composition in a dosage form comprising a tablet sized for placement under a tongue, wherein the pharmaceutical composition comprises
   (a) carrier particles having exterior surfaces,
   (b) particles of zolpidem or a pharmaceutically acceptable salt thereof sized smaller than the carrier particles and presented, at least in part, upon the exterior surfaces of the carrier particles and said particles of zolpidem or salt thereof cover at least 90% of the exterior surfaces of said carrier particles; and
   (c) particles of a mucoadhesion promoting agent sized smaller than the carrier particles and presented, at least in part, upon the exterior surfaces of the carrier particles, wherein both the particles of zolpidem or a pharmaceutically acceptable salt thereof and the particles of the mucoadhesion promoting agent are presented, at least in part, upon the exterior surfaces of the carrier particles; and
   sublingually administering the pharmaceutical composition to the individual to treat the insomnia by placing the tablet under the tongue of the individual, wherein sublingual administration of the pharmaceutical composition provides a therapeutic outcome comprising
   (i) a measurable plasma concentration of zolpidem within 10 minutes of sublingual administration; and
   (ii) a time difference following sublingual administration between a first measurable plasma concentration of zolpidem and a maximum measured plasma concentration of zolpidem that is within a range of about 80 minutes to about 160 minutes; and
   (iii) a plasma concentration of zolpidem that is capable of maintaining sleep for at least about 6 hours after sublingual administration; wherein
   said individual is thereby treated for insomnia.

2. A method according to claim 1 wherein the insomnia comprises transient insomnia.

3. A method of providing sleep on demand to an individual by sublingual administration of a pharmaceutical composition, the method comprising
   providing the pharmaceutical composition in a dosage form comprising a tablet sized for placement under a tongue, wherein the pharmaceutical composition comprises
   (a) carrier particles having exterior surfaces,
   (b) particles of zolpidem or a pharmaceutically acceptable salt thereof sized smaller than the carrier particles and presented, at least in part, upon the exterior surfaces of the carrier particles and said particles of zolpidem or salt thereof cover at least 90% of the exterior surfaces of said carrier particles; and
   (c) particles of a mucoadhesion promoting agent sized smaller than the carrier particles and presented, at least in part, upon the exterior surfaces of the carrier particles, wherein both the particles of zolpidem or a pharmaceutically acceptable salt thereof and the particles of the mucoadhesion promoting agent are presented, at least in part, upon the exterior surfaces of the carrier particles; and
   sublingually administering the pharmaceutical composition to the individual to treat the insomnia by placing the tablet under the tongue of the individual, wherein sublingual administration of the pharmaceutical composition provides a therapeutic outcome comprising
   (i) a measurable plasma concentration of zolpidem within 10 minutes of sublingual administration; and
   (ii) a time difference following sublingual administration between a first measurable plasma concentration of zolpidem and a maximum measured plasma concentration of zolpidem that is within a range of about 80 minutes to about 160 minutes; and
   (iii) a plasma concentration of zolpidem that is capable of maintaining sleep for at least about 6 hours after sublingual administration; wherein
   said individual is thereby provided with sleep on demand.

4. A method according to claim 1 or 3
   wherein at least 50% of the zolpidem that is present in the pharmaceutical composition upon sublingual administration is released within 5 minutes, as tested and measured in a standard in vitro paddle apparatus according to the United States Pharmacopoeia, using a phosphate buffer at pH 6.8 (USP) as dissolution medium.

5. A method according to claim 4
   wherein at least 50% of the zolpidem that is present in the pharmaceutical composition upon administration is released within 3 minutes.

6. A method according to claim 1 or 3
   wherein the therapeutic outcome further provides (iv) a plasma concentration of zolpidem that does not result in decreased alertness and/or impairment of psychomotor function in a patient following sleep at least about 7 hours after sublingual administration.

7. A method according to claim 1 or 3
   wherein the salt of zolpidem is zolpidem hemitartrate.

8. A method according to claim 1 or 3
   wherein the particles of zolpidem or pharmaceutically-acceptable salt thereof are microparticles.

9. A method according to claim 8
   wherein the microparticles have a weight based mean diameter of between about 1 µm and about 10 µm.

10. A method according to claim 1 or 3
    wherein the zolpidem or a pharmaceutically acceptable salt thereof comprises between about 5 to about 15 weight percent of the pharmaceutical composition.

11. A method according to claim 1 or 3
    wherein the pharmaceutical composition comprises about 5 mg to about 12 mg of zolpidem or a pharmaceutically acceptable salt thereof in a dose unit of the pharmaceutical composition.

12. A method according to claim 1 or 3
    wherein the mucoadhesion promoting agent is sodium carboxymethylcellulose.

13. A method according to claim 12 wherein the sodium carboxymethylcellulose is internally crosslinked sodium carboxymethylcellulose (croscarmellose sodium).

14. A method according to claim 1 or 3 wherein the mucoadhesion promoting agent comprises between about 3.5 to about 6.5 weight percent of the pharmaceutical composition.

15. A method according to claim 1 or 3 wherein the pharmaceutical composition further comprises a binder or disintegrating agent.

16. A method according to claim 15 wherein the binder is microcrystalline cellulose.

17. A method according to claim 16 wherein the microcrystalline cellulose is silicified microcrystalline cellulose.

18. A method according to claim 15 wherein the binder comprises between about 2.0 to about 3.0 weight percent of the pharmaceutical composition.

19. A method according to claim 1 or 3 wherein the carrier particles have a weight based mean diameter of between about 150 µm to about 400 µm.

20. A method according to claim 1 or 3 wherein the carrier particles comprise mannitol.

21. A method according to claim 20 wherein the mannitol is spray-dried mannitol.

22. A method according to claim 1 or 3 wherein the carrier particles comprise between about 70 to about 85 weight percent of the pharmaceutical composition.

23. A method according to claim 1 or 3 wherein the coverage is between about 130% and about 180%.

24. A method according to claim 1 or 3 wherein the pharmaceutical composition further comprises a lubricant.

25. A method according to claim 24 wherein the lubricant is magnesium stearate.

26. A method according to claim 1 or 3 wherein the tablet has a weight of about 80 mg and a diameter of about 6 mm.

* * * * *